United States Patent
Ren et al.

(10) Patent No.: US 11,531,027 B2
(45) Date of Patent: Dec. 20, 2022

(54) LOW COST DISPOSABLE MEDICAL SENSOR FABRICATED ON GLASS, PAPER OR PLASTICS

(71) Applicant: University of Florida Research Foundation, Inc., Gainesville, FL (US)

(72) Inventors: Fan Ren, Gainesville, FL (US); Stephen J. Pearton, Gainesville, FL (US)

(73) Assignee: UNIVERSITY OF FLORIDA RESEARCH FOUNDATION, INC., Gainesville, FL (US)

( * ) Notice: Subject to any disclaimer, the term of this patent is extended or adjusted under 35 U.S.C. 154(b) by 383 days.

(21) Appl. No.: 16/206,493

(22) Filed: Nov. 30, 2018

(65) Prior Publication Data

US 2019/0170738 A1    Jun. 6, 2019

Related U.S. Application Data

(60) Provisional application No. 62/593,552, filed on Dec. 1, 2017.

(51) Int. Cl.
*G01N 33/543*    (2006.01)
*H01L 29/778*    (2006.01)
(Continued)

(52) U.S. Cl.
CPC ..... *G01N 33/5438* (2013.01); *G01N 33/6887* (2013.01); *H01L 29/778* (2013.01);
(Continued)

(58) Field of Classification Search
CPC .......... G01N 33/5438; G01N 33/6887; G01N 27/4145; H01L 29/778; H01L 29/7786; H01L 29/2003
See application file for complete search history.

(56) References Cited

U.S. PATENT DOCUMENTS 4,464,581 A    8/1984    Oritani
9,316,637 B2    4/2016    Ren
(Continued)

FOREIGN PATENT DOCUMENTS

CN    104024841 A    *    9/2014    ......... G01N 27/4145
CN    107121544 A    *    9/2017
(Continued)

OTHER PUBLICATIONS

Shukla, Shruti, et al. "Rapid Detection Strategies for the Global Threat of Zika Virus: Current State, New Hypotheses, and Limitations", Oct. 2016, Frontiers in Microbiology, 7:1685. (Year: 2016).*
(Continued)

*Primary Examiner* — Matthew D Krcha
*Assistant Examiner* — Henry H Nguyen
(74) *Attorney, Agent, or Firm* — Thomas | Horstemeyer, LLP

(57) ABSTRACT

Various examples are provided for low cost disposable medical sensors fabricated on glass, paper or plastics, and applications thereof. In one example, a medical sensor includes a base structure comprising a functionalized sensing area; and a transistor disposed on the base structure adjacent to the functionalized sensing area. In another example, a medical sensor includes a base structure comprising a functionalized sensing area disposed on a first electrode pad and a reference sensing area disposed on a second electrode pad separated from the first electrode pad; and a transistor having a gate electrically coupled to the second electrode pad of the base structure. A gate pulse applied to the functionalized sensing can produce a drain current corresponding to an amount of a target present in a sample disposed on the base structure.

13 Claims, 8 Drawing Sheets

(51) Int. Cl.
*G01N 33/68* (2006.01)
*H01L 29/20* (2006.01)
*G01N 27/414* (2006.01)

(52) U.S. Cl.
CPC ...... *G01N 27/4145* (2013.01); *H01L 29/2003* (2013.01); *H01L 29/7786* (2013.01)

(56) References Cited

U.S. PATENT DOCUMENTS

| | | | |
|---|---|---|---|
| 2010/0188069 A1* | 7/2010 | Ren | G01N 27/4145 324/71.5 |
| 2011/0088456 A1* | 4/2011 | Ren | H01L 29/42316 73/31.06 |
| 2015/0160285 A1* | 6/2015 | Joh | G01R 31/2621 324/754.03 |
| 2015/0276667 A1* | 10/2015 | Klootwijk | G01N 27/4148 506/9 |
| 2015/0355129 A1* | 12/2015 | Knopfmacher | G01N 27/3272 205/792 |
| 2017/0234830 A1* | 8/2017 | White | C12Q 1/6869 205/775 |
| 2017/0350852 A1 | 12/2017 | Lee | |
| 2019/0170738 A1 | 6/2019 | Ren | |

FOREIGN PATENT DOCUMENTS

| | | | |
|---|---|---|---|
| KR | 20150111395 A | * | 10/2015 |
| WO | WO-2014088263 A1 | * | 6/2014 ........ G01N 27/127 |
| WO | WO-2017153909 A1 | * | 9/2017 | |

OTHER PUBLICATIONS

Sarangadharan, Indu, et al., "High sensitivity cardiac troponin I detection in physiological environment using AlGaN/GaN High Electron Mobility Transistor (HEMT) Biosensors", Sep. 2017, Biosensors and Bioelectronics, 100, p. 282-289. (Year: 2017).*
Hsu, Chen-Pin, et al., "A Package Technology for Miniaturized Field-Effect Transistor-Based Biosensors and the Sensor Array", Apr. 2017, ECS J. Solid State Sci. Technol. (Year: 2017).*
Spiegel et al. (Spiegel et al., "The Extended Gate Chemically Sensitive Field Effect Transistor as Multi-Species Microprobe", 1983, Sensors and Actuators, 4, 291-298). (Year: 1983).*
Guan et al. (Guan et al., "Extended Gate Field-Effect Transistor Biosensors for Point-Of-Care Testing of Uric Acid", Mar. 2017, Biosensors and Biodetection, pp. 189-203) (Year: 2017).*
Guan et al., "Highly specific and sensitive non-enzymatic determination of uric acid in serum and urine by extended gate field effect transistor sensors", Jan. 2014, Biosens Biuoelectron., 15:255-31 (Year: 2014).*
International search report for PCT/US20/55900 dated Jan. 19, 2021.
Yang, et al., "Rapid detection of cardiac troponin I using antibody immobilized gate pulsued AlGaN/GaN high election mobility transistor structures", Appl. Phys. Lett. 111, 202104 (Nov. 2017).

* cited by examiner

LOW COST DISPOSABLE MEDICAL SENSOR FABRICATED ON GLASS, PAPER OR PLASTICS

CROSS REFERENCE TO RELATED APPLICATIONS

This application claims priority to, and the benefit of, U.S. provisional application entitled "Low Cost Disposable Medical Sensor Fabricated on Glass, Paper or Plastics" having Ser. No. 62/593,552, filed Dec. 1, 2017, which is hereby incorporated by reference in its entirety.

STATEMENT REGARDING FEDERALLY SPONSORED RESEARCH OR DEVELOPMENT

This invention was made with government support under grant number 1439644 awarded by the National Science Foundation (NSF). The government has certain rights in the invention.

BACKGROUND

Cardiac troponin I (cTnI) and the complex involving cTnI, cardiac troponin T (cTnT), and cardiac troponin C (cTnC) in the cardiac muscle tissue are the standard clinical biomarkers for Acute Myocardial Infarction (AMI) and diseases that produce cardiac muscle damage. The concentrations of these species rises quickly in the blood following the onset of AMI as they are released from myocardial cells following cell death.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

DETAILED DESCRIPTION

Figure 1A:
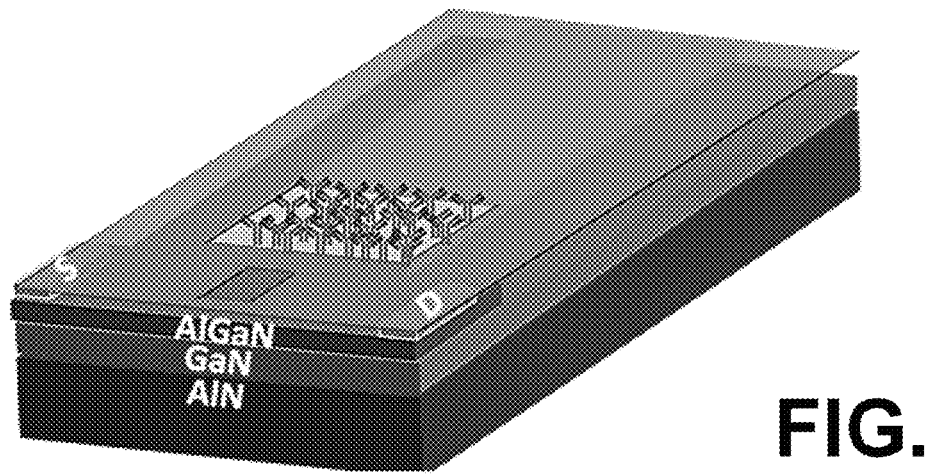
FIGS. 1A and 1B are schematics illustrating examples of a dipping sensor and a cover glass sensor, in accordance with various embodiments of the present disclosure.

Disclosed herein are various embodiments related to low cost disposable medical sensors fabricated on glass, paper or plastics, and applications thereof. Reference will now be made in detail to the description of the embodiments as illustrated in the drawings, wherein like reference numbers indicate like parts throughout the several views.

Elevated troponin concentrations can be detected in the blood within a few hours up to several days following the onset of angina (where myocardial cells suffer reversible damage) to AMI where myocardial cells die. The time-dependence of concentration of these species is commonly detected by antigen-antibody or apatamer-based interactions using techniques such as radioimmunoassay, enzyme-linked immunosorbent assay (ELISA) fluorimetric, luminometric, colorimetric, and amperometric (electrochemical) methods.

Many of these are time consuming and require trained personnel to perform tests. The challenge is to develop a real-time, accurate, handheld and low cost heart attack sensor. The measurement of blood troponin concentrations can decide whether AMI has occurred or that chest pain and other symptoms are due to other causes. Inexpensive techniques that provide rapid, accurate blood troponin concentrations would be welcome in managing treatment of patients in emergency room situations.

A comparison of two different approaches to detecting cardiac troponin I (cTnI) using antibody-functionalized AlGaN/GaN High Electron Mobility Transistors (HEMTs) is examined. If the solution containing the biomarker has high ionic strength, there can be difficulty in detection due to charge-screening effects. To overcome this, a first method involving pulsed biases applied between a separate functionalized electrode and the gate of the HEMT can be utilized. The resulting electrical double layer produces charge changes which can be correlated to the concentration of the cTnI biomarker. A second approach fabricates the sensing area on a glass slide, with the pulsed gate signal externally connected to the nitride HEMT. This produces a larger integrated change in charge and can be used over a broader range of concentrations without suffering from the charge screening effects. Both approaches can detect cTnI at levels down to about 0.01 ng/ml. The cover glass slide approach is attractive for inexpensive cartridge-type sensors. Besides glass slides, plastics and paper can also be used as the disposable functionalized sensor strips.

With this approach, any transistor technology, such as Si metal oxide semiconductor field effect transistor (MOSFETs), complementary MOSFETs (CMOSFETs), FinFETs, heterostructure high electron mobility transistors (HEMTs), bipolar transistors, or heterojunction bipolar transistors (HBTs), can be placed in the sensing package to amplify the pulsed signal from functionalized glass slide. The disclosed sensor technology can be functionalized with an antibody, ceramics, enzymes, peptides, proteins, DNA or aptamer for breast cancer, glucose, pH, prostate specific antigen, lung cancer, Zika, etc. for medical applications, pathogen, anthrax, ricin for toxicant detection and ammonia, oxygen, carbon monoxide, carbon dioxide, nitrous oxide and hydrogen for gas detection applications.

Zika virus detection is also examined using antibody-functionalized cover glasses externally connected to the gate electrode of an AlGaN/GaN high electron mobility transistor (HEMT). A pulsed bias voltage of 0.5V was applied to an electrode on the region of the cover glass region functionalized with antibody, and the resulting changes of drain current of the HEMT were employed to determine the presence of Zika virus antigen concentration ranging from 0.1 to 100 ng/ml. The dynamic and static drain current changes as a function of Zika virus concentration can be modeled with a spring-like elastic relaxation model and the Langmuir extension model, respectively. Excellent fits to the data were found with relaxation time constants of antibody and antigen molecules in the range of 11 Is and 0.66-24.4 Is, respectively, for the concentration range investigated. The ratio of antibody bound with antigen to the total available antibody on the functionalized contact window was in the range of 0.013-0.84 for the Zika antigen concentration range of 0.1-100 ng/ml. Since the HEMT is not exposed to the bio-solution, it can be used repeatedly. The functionalized glass is the only disposable part in the detection system, showing the potential of this approach for hand-held, low cost sensor packages for point-of-care applications.

Detection of Cardiac Troponin I

Cardiac troponin I (cTnI) and the complex involving cTnI, cardiac troponin T (cTnT), and cardiac troponin C (cTnC) in the cardiac muscle tissue are the standard clinical biomarkers for Acute Myocardial Infarction (AMI) and diseases that produce cardiac muscle damage. The concentrations of these species rises quickly in the blood following the onset of AMI as they are released from myocardial cells following cell death. Elevated troponin concentrations can be detected in the blood within a few hours up to several days following the onset of angina (where myocardial cells suffer reversible damage) to AMI where myocardial cells die. The time-dependence of concentration of these species is commonly detected by antigen-antibody or apatamer-based interactions using techniques such as radioimmunoassay, enzyme-linked immunosorbent assay (ELISA) fluorimetric, luminometric, colorimetric, and amperometric (electrochemical) methods. Many of these are time consuming and require trained personnel to perform tests. The challenge is to develop a real-time, accurate, handheld and low cost heart attack sensor. The measurement of blood troponin concentrations can be used to determine whether AMI has occurred or that chest pain and other symptoms are due to other causes. Inexpensive techniques that provide rapid, accurate blood troponin concentrations would be welcome in managing treatment of patients in emergency room situations.

Field-effect transistors (FETs) functionalized with antibodies or apatamer layers in the gate region, often referred to as bio-FETs, can be effective sensors for a variety of biomarkers. In particular, AlGaN/GaN high electron mobility transistors (HEMTs) offer an attractive option. Due to spontaneous and piezoelectric polarization, a two dimensional electron gas (2DEG) channel exists at the interface between AlGaN and GaN, and the carrier conductivity at the 2DEG channel is very sensitive to surface charge changes on the gate region. HEMTs with a higher channel conductivity can show a better sensitivity for biomarker detection. With 30% Al concentration in AlGaN layer, 5-10 times higher sheet electron densities can be obtained compared to GaAs or InP HEMTs. Also, the intrinsic carrier concentration of GaN is $10^{-10}$ $cm^{-3}$ while that of Si is $10^{10}$ $cm^{-3}$, which enables stable operation of the sensor at higher temperatures. Improved detection limits can be obtained with differential-mode HEMT biosensors employing an Au-gate HEMT as the sensing device to react with biomolecules, while a separate Pt-gate HEMT can be used as the dummy device in the differential-mode detection circuit. Both the biosensing HEMT and reference HEMT can be biased by a Pt quasi-reference electrode.

An electrical double layer gated high field AlGaN/GaN HEMT biosensor can be used in which the gating mechanism overcomes charge screening effects that are prevalent in traditional FET based biosensors, allowing detection of target proteins in physiological solutions. It is possible to detect troponin I in blood samples at low concentrations and wide dynamic range (0.006-148 ng/mL), using both antibody and apatamer functionalization. In this design, when the gate electrode is positively biased, negative ions accumulate on the surface of the open area on the gate electrode. Similarly, positive ions accumulate on the open area of the channel, resulting in increased carrier density in the 2DEG. An electronic double layer forms on the gate metal and the surface of the channel. Introduction of a solution on the top of the HEMT changes the capacitance of the effective gate dielectric and if this capacitance changes due to binding reactions, the voltage in solution drops and the gate voltage also changes, resulting in a change in drain current.

In this disclosure, an investigation of two testing techniques using AlGaN/GaN HEMTs to detect cTnI is reported. For a first dipping sensor, the gate electrode area can be electrically connected to a nearby area functionalized with the troponin antibody. This functionalized electrode can be spaced apart from the gate of the HEMT, with the biomarker introduced into contact with the gate and the reactive electrode. A pulsed voltage can be applied between the reactive electrode and the source and the resulting current recorded.

In the second approach, a HEMT connected to a cover glass with functionalized and reference areas. The functionalized area can again be subjected to voltage pulses, while the reference area is connected to the gate of the HEMT. Then, bias pulses can be applied to the gate side and the drain terminal and the total accumulated charge calculated from the monitored response current. This voltage pulsing changes the ion distribution in the solution and leads to changes in drain current. It is shown that this latter approach is advantageous in providing a larger current and charge change for detection as well as being more versatile in terms of miniaturized sensor designs.

The AlGaN/GaN HEMT structures were grown on AlN low temperature layers on c-axis sapphire substrates with 2.2 μm of undoped GaN and 25 nm of $Al_{0.25}Ga_{0.75}N$ by metal organic chemical vapor deposition. Inductively coupled plasma (ICP) etching was used to remove 110 nm of material for device isolation ($Cl_2$/Ar, 200 W (2 MHz) source power and 50 W RF (13.56 MHz) chuck power at 5 mTorr, about 150 V of DC bias voltage on the chuck electrode). The source and drain Ohmic contact pads were metalized by lift-off of E-beam evaporated Ti/Al/Ni/Au (25/125/45/100 nm) and then annealed at 850° C. for 45 s in $N_2$. Source, drain and gate electrodes were patterned by lift-off of Ti/Au (20/80 nm).

To perform the surface functionalization in which the functional layer is on the HEMT itself, a 100 nm $SiN_X$ passivation layer was deposited on the entire wafer. A square opening (100×120 μm) on the gate electrode and active gate channel area (10×50 μm) 30 μm apart were opened using lithography. To immobilize the Anti-Cardiac Troponin I antibody, thioglycolic acid (TGA, $HSCH_2COOH$) was used as a binding agent between the gold surface and antibody molecule. The gate electrode was exposed to TGA solution for functionalization. The sample surface was treated with Ozone (10 min) to remove carbon contamination on the exposed Au surface before thioglycolic acid treatment. Then, the lithographically exposed gate electrode was functionalized with 1 mM of TGA solution for 12 hours. The TGA side group thiol group strongly interacts with and bonds to the Au, self-assembles to form a TGA monolayer on the Au and exposure of carboxylic group (another TGA side group) produces a further chemical linking reaction to the antibodies. The wafer was rinsed with de-ionized wafer to remove excess TGA and then acetone to strip the resist. The Anti-Cardiac Troponin I antibody (100 μg/ml) was introduced to wafer surface, and the sample was stored at 4° C. for three hours to immobilize the antibody. The wafer was rinsed with 10 mM PBS solution to remove un-bonded antibody from the wafer surface. FIG. 1A shows a schematic illustrating an example of the dipping sensor after functionalization of this first approach. The dipping sensor comprises a functionalized area on the channel placed at a small distance from the gate electrode.

Figure 1B:
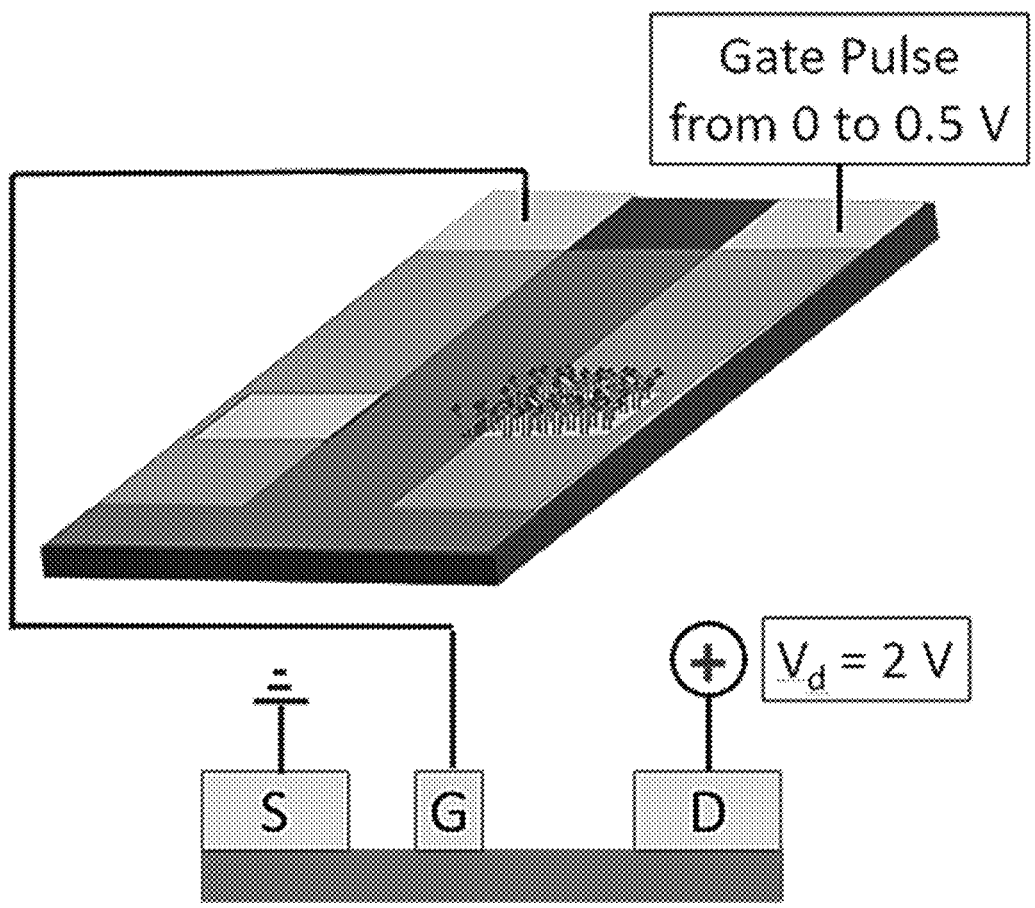

The second cover glass approach differs by incorporating formation of Schottky contacts by E-beam deposition of Ni/Au (20 nm/80 nm). FIG. 1B shows a schematic of a cover glass sensor using the second approach after functionalization, and with the connections between cover glass and FET device. On the cover glass, separated (20 μm separation) metal lines (Ni/Au; 20 nm/80 nm) were formed by lithography and E-beam deposition. Only one of the openings on the cover glass is functionalized with antibody, while the other acts as a reference. The gate can be pulsed from 0 to 2V, while the drain voltage is held at 2V.

For detection of cTnI, drain currents were measured at 25° C. using an Agilent B1500 parameter analyzer with Be/Cu probe tips. The Agilent B1530 pulse generator was also used to generate a step waveform function for both gate and drain electrodes, with an 8 μs delay period for both pulse signals. The HEMT was biased with 2 V on the drain and 0 V on the gate for 2 μs. Then, 0.5 V was applied to the gate for 50 μs while keeping the drain bias at 2 V. Once the gate voltage dropped to 0 V, the drain was biased for extra 5 μs before it dropped to 0 V. The rise and fall time for each pulse function was about 80 ns. The targeted Natural Cardiac Troponin I protein concentrations were 0.1 μg/ml, 1 μg/ml, 10 μg/ml, and 100 ng/ml in 1×PBS with 1% BSA. The level of cTnI in AMI patients is around 10 ng/ml and can go up to 10 to 550 ng/ml. For early detection of AMI patients, the cTnI concentration is in the range 0.5 to 2.0 ng/ml. Before each measurement for individual target concentrations, there was five minutes of the buffering time for the Natural Cardiac Troponin I protein to bind to the Anti-Cardiac Troponin I antibody.

The cover glass approach employed the same 2 V bias on the drain, with the gate electrode connected to the un-functionalized Au electrode. The functionalized side of gold electrode was connected to the pulse generator. The functionalized side of the gold electrode is labelled the cover glass active electrode. The pulse generator produced a step waveform function for both cover glass active and drain electrodes. There was the same 8 μs delay period for both pulse signals, then the HEMT was biased at 2 V drain electrode and 0 V to the cover glass active electrode for 2 μs. Then, 0.5 V of voltage was applied to the cover glass active electrode for 50 μs while keeping the drain biased voltage at 2 V. Once the cover glass active bias voltage dropped to 0 V, the drain electrode was biased for extra 5 μs before it was reduced to 0 V.

Figure 2A:
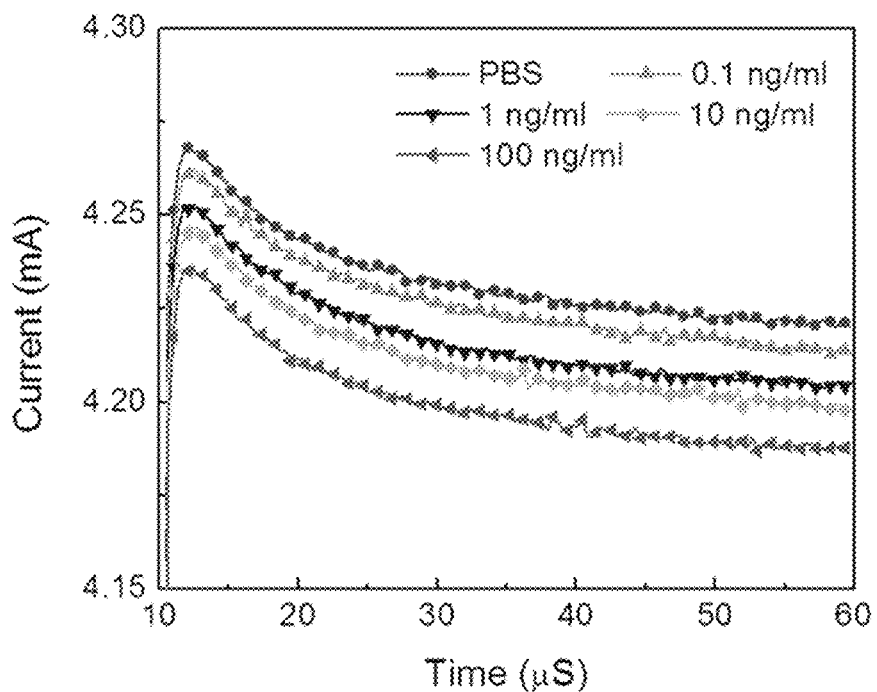
FIGS. 2A and 2B illustrate examples of drain current response using the dipping sensor of FIG. 1A and the cover glass sensor of FIG. 1B, respectively, in accordance with various embodiments of the present disclosure.
Figure 2B:
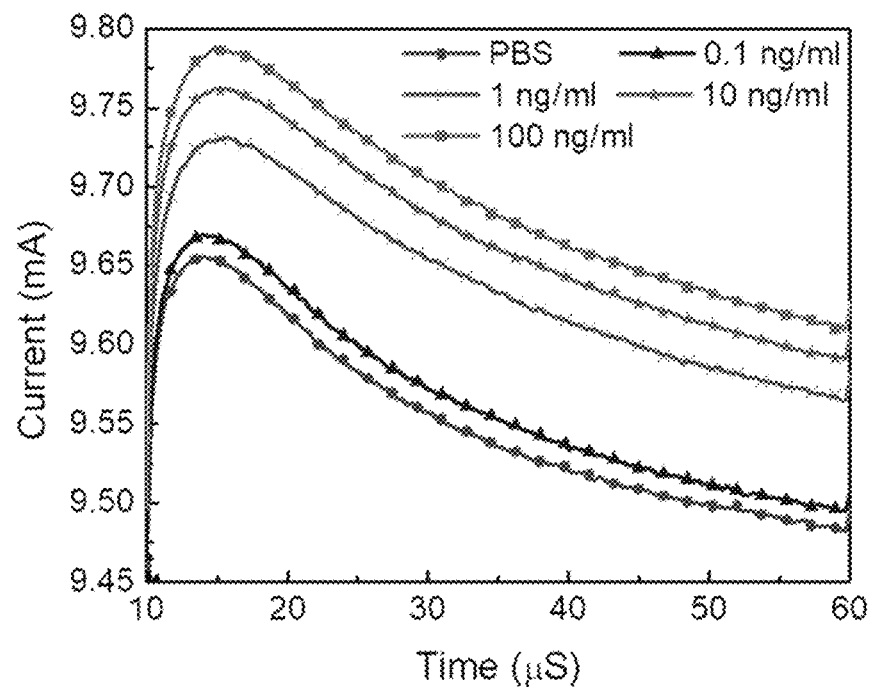

Referring to FIGS. 2A and 2B, shown are examples of the drain current response with different cTnI concentrations using either the dipping sensor approach or the cover glass approach, respectively. FIG. 2A shows the drain current characteristics of the dipping sensor of FIG. 1A with different troponin concentrations. The troponin causes a decrease in current relative to standard PBS solution. The analysis of the electrical double layer formed during the pulsed biasing of functionalized HEMTs has also been previously discussed. By contrast, the cover glass approach leads to an increase in the pulsed current, as shown in FIG. 2B. In this configuration, the receptor immobilization produces a decrease in total capacitance of the solution plus dielectric capacitance and thus a decrease in effective gate voltage and an increase in current.

Figure 3:
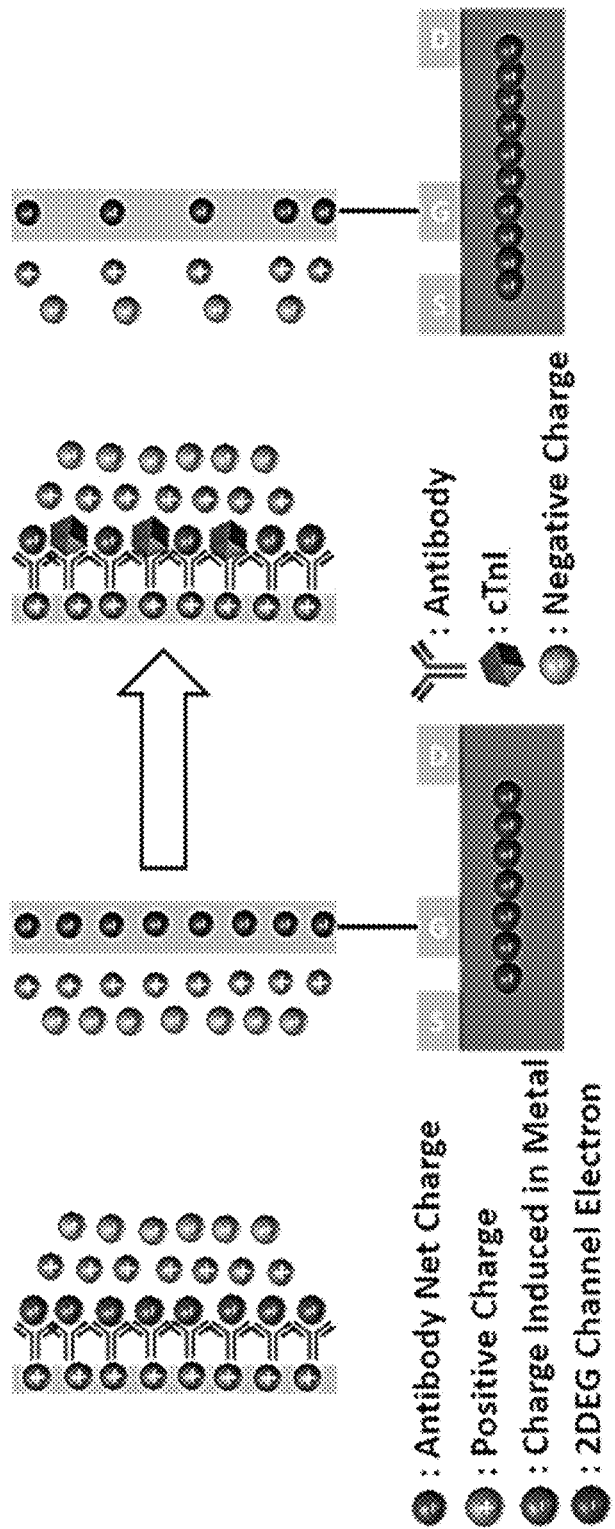
FIG. 3 illustrates charge and current changes as a result of antigen-antibody binding in the sensors of FIGS. 1A and 1B, in accordance with various embodiments of the present disclosure.

The larger change in the signal from the glass sensor results from the higher fall-off of field and higher charge induced on the AlGaN surface in this configuration. The charge and current changes as a result of antigen-antibody binding in the two types of sensors is illustrated schematically in FIG. 3. The sign of the current change depends on field distribution, ion mobility, relaxation times and concentration. The integrated current (the charge) provides a superior measure of the biosensor response.

The sensing mechanism is the binding of the antibody to the receptor, which can be assumed to be a reversible reaction whose dissociation constant follows a one site binding model. The measured changes in current for different concentrations of Troponin I protein in 1×PBS with 1% BSA are summarized in the following table.

| CTnI Concentration (ng/ml) | Dipping sensor ΔI (μA); Total Charge (nC) | Cover plate sensor ΔI (μA); Total Charge (nC) |
| --- | --- | --- |
| 0 (PBS) | 0; 210.1 | 0; 478.0 |
| 0.1 | −8.6; 209.7 | 14.6; 478.8 |
| 1 | −19.4; 209.3 | 87.8; 482.5 |
| 10 | −25.3; 209.0 | 116.2; 483.9 |
| 100 | −36.7; 208.5 | 137.7; 485.0 |

Figure 4A:
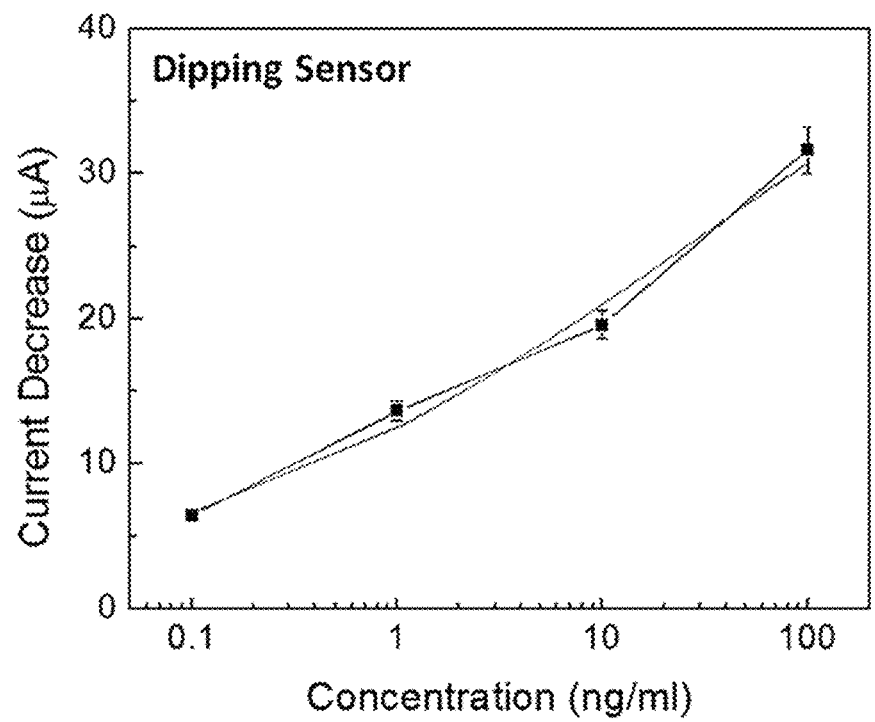
FIGS. 4A and 4B illustrate experimental values of current with one site binding model fitting using the dipping sensor of FIG. 1A and the cover glass sensor of FIG. 1B, respectively, in accordance with various embodiments of the present disclosure.
Figure 4B:
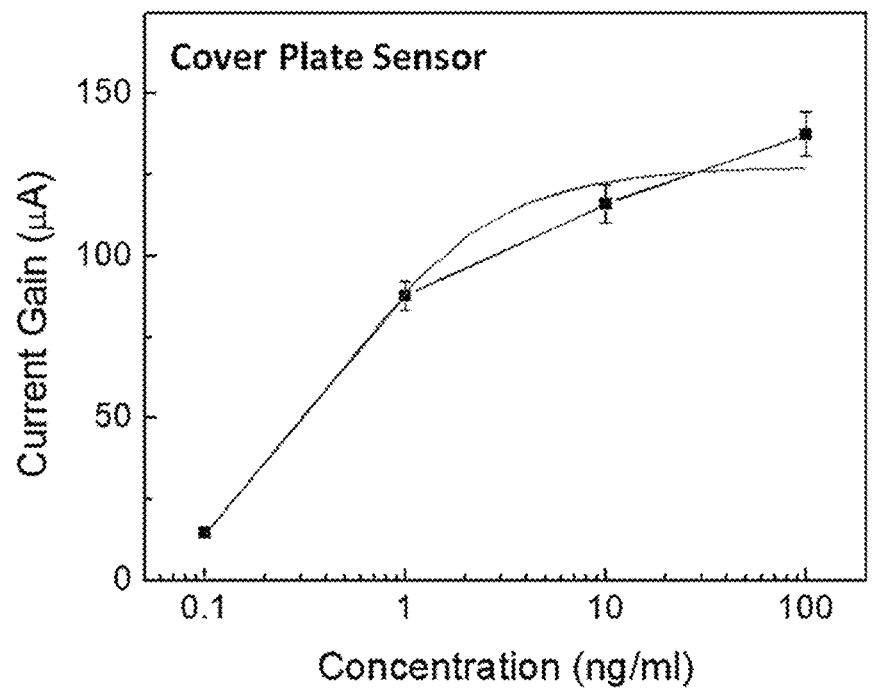

FIGS. 4A and 4B show the experimental values of current change for different concentration of Troponin I protein in a 1×PBS with 1% BSA for the dipping sensor and the cover glass sensor, respectively, as well as one site model fit. The model fitting for this set of data is based on the Langmuir Extension model with:

$$\Delta I = \frac{a*b*[C]^{(1-d)}}{1+b*[C]^{(1-d)}}, \quad (1)$$

where ΔI is the change in drain current with unit of μA, [C] is the antigen concentration [ng/ml], and constants a, b, and d. The model fitting for this data set produced the following relations:

$$\Delta I = \frac{14.14*[C]^{0.29}}{1+0.14*[C]^{0.29}} \quad (2)$$

for the dipping sensor in FIG. 4A, and:

$$\Delta I = \frac{184*[C]^{1.08}}{1+1.84*[C]^{1.08}} \quad (3)$$

for the cover glass sensor in FIG. 4B. The good fits to the experimental data show that the one site approximation is reasonable in this case.

The sensitivity can be enhanced and effects of random noise reduced by calculating the total charge accumulated on the HEMT surface by integrating the drain current over time. Since the change in current as a result of antigen-antibody binding is related to the time rate of change of charge, $$I = \frac{\partial Q}{\partial t}, \quad (4)$$

the total charge can be calculated by integration of the current curve from the drain current response to different Troponin I concentration. The PBS data point was not included in this figure because it is plotted in semi-log scale.

Figure 5A:
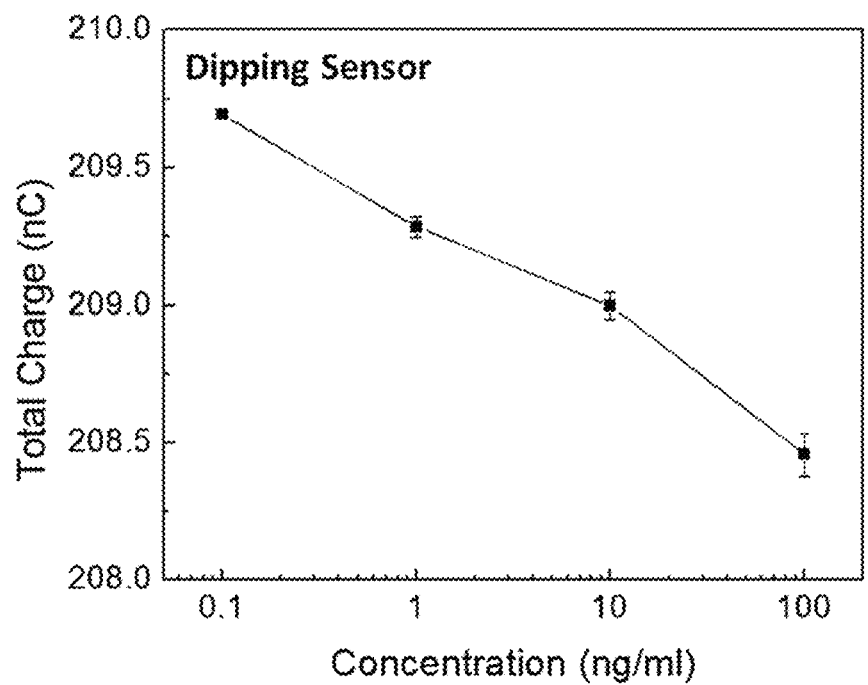
FIGS. 5A and 5B illustrate examples of the relationship of total charge for the dipping sensor of FIG. 1A and the cover glass sensor of FIG. 1B, respectively, in accordance with various embodiments of the present disclosure.
Figure 5B:
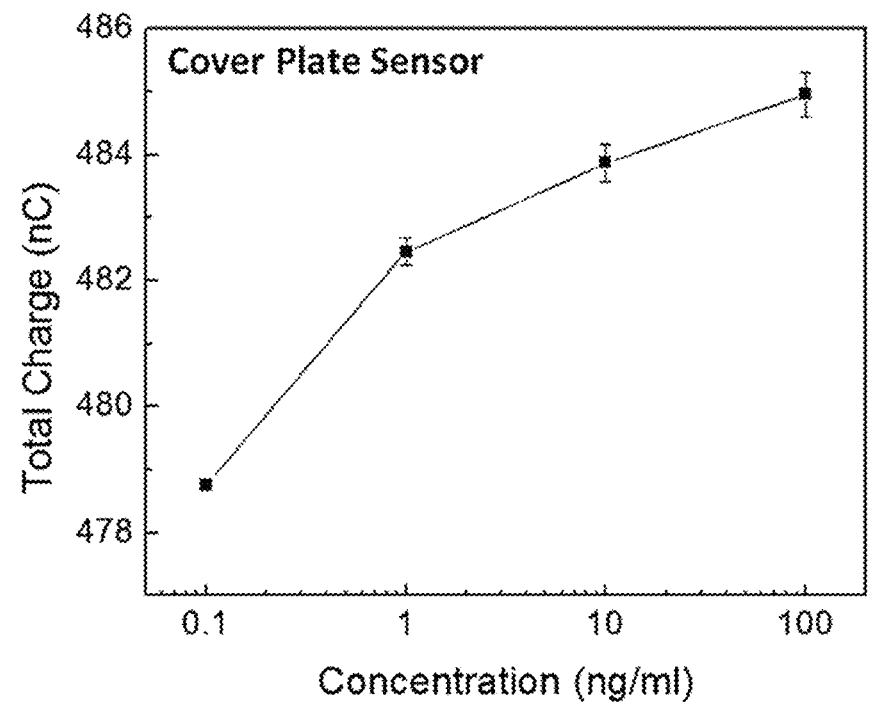

FIGS. 5A and 5B illustrate examples of the relationship of total charge to different Troponin I protein concentrations of 0.1 ng/ml, 1 ng/ml, 10 ng/ml, and 100 ng/ml in 1×PBS and 1% BSA solutions for the dipping sensor and cover glass sensor, respectively. The charge variations are approximately in proportion to the logarithmic biomarker concentration in the liquid sample. The charge accumulated at the biosensor within a pulse width of an applied voltage pulse can be correlated to the analyte concentration in the liquid sample applied to the HEMT. Conventional HEMTs with the antibody immobilized on the gate region above the active channel have high charge screening effect in high ionic strength solutions, such as serum or blood, reducing protein detection sensitivity in physiological environments where the Debye length is much smaller than the antibody. The electronic double layer approaches described here do not need dilution to reduce the ionic strength. It should be noted that the ability to use a glass slide to contain the functionalized area is attractive for the viewpoint of having an inexpensive, disposable cartridge approach in sensor designs in which the HEMT itself remains as part of the electronic package.

In summary, Cardiac troponin-I (cTnI) released from damaged heart muscle is an effective biomarker for acute myocardial infraction (AMI) in terms of specificity and sensitivity, and the development of simplified, electronic-based rapid sensors is desirable. The electronic double layer HEMT designs described here enhance the current gain of the sensor in high ionic strength solutions, resulting in increased sensitivity and specificity in detection of Troponin I. The ability to use a simple, functionalized glass slide as the active sensing area opens up the possibility of inexpensive cartridge sensor designs. Besides glass slides, plastics and paper can also be used as the disposable functionalized sensor strips.

Detection of Zika Virus

The Zika virus (ZIKV) is a flavivirus similar to West Nile virus, dengue, or yellow fever. The virus is primarily transmitted via the *Aedes* mosquito. Zika has been associated with improper brain development in fetuses—retinopathy, brain calcification, and microcephaly. The ZIKV is a positive single stranded RNA with an open reading frame of 50-C-prM-E-NS1-NS2A-NS2B-NS3-NS4A-NS4b-NS5-30. The NS1 protein was selected as the appropriate target for sensing, as it is excreted from infected cells in the form of a trimer and is found in the plasma membrane of infected cells. The NS1 protein's function is related to flaviviral replication, immune evasion, and pathogenesis; however, the exact function is not understood and has only been extrapolated recently from comparison to the NS1 protein in West Nile and Dengue. The structure of the ZIKV has been well documented with the recent advances in cryo-electron microscopy, which obtained a few A level resolution. These advances allow for detailed analysis of protein folding, mapping, and initial investigations into the individual protein function. Currently, no treatment is available for affected individuals with Zika other than bed rest, hydration, and nutrition.

It has been shown that ZIKV can be detected by using RNA in human urine, serum, and saliva specimens using the reverse transcription polymerase chain reaction (RT-PCR) method. However, the detection results were only robustly positive for urine testing using this highly sensitive RT-PCR method. Another ZIKV detection method has focused on testing of human saliva, with the peptidome analysis using mass spectrometry (MS/MS). Yet, when using PCR to identify a specific structural protein in the saliva for detection, there were no positive results from this testing due to the degradation of RNA in saliva during the saliva collection, storage, and processing. Reverse transcription loop-mediated isothermal amplification (RT-LAMP) was also used to detect ZIKV RNA in unprocessed biological samples like urine, plasma, and Zika infected mosquito carcasses, with a detection limit of 0.71 pfu. All of these methods are time consuming and require a well-trained technician to perform and complete the tests. Thus, there is a need for a rapid and reliable ZIKV detection technique. A reliable bio-sensor that would provide rapid, accurate blood ZIKV concentration without any centrifuge and dilution would be a ground-breaking technology for determining whether a patient is infected with the ZIKV.

An electronic detection approach is possible for viruses, using biologically functionalized field effect transistors (bio-FETs). The graphene-based field effect biosensor will be demonstrated for Zika Virus detection with an antibody and antigen interaction mechanism. An attractive approach is the use of AlGaN/GaN high electron mobility transistors (HEMTs) functionalized with antibody or aptamer over the active gate channel. The AlGaN/GaN HEMTs have demonstrated superior bio-sensing characteristics due to a high density two-dimensional electron gas (2DEG) channel located close the surface (around 25 nm) and very sensitive to changes in surface a) charges. However, for conventional AlGaN/GaN HEMT bio-sensing applications with the antibody immobilized directly over the active gate channel, the detection would not be very consistent for high ionic strength solutions such as human blood or serum. This is due to the high charge screening effect in high ionic strength solutions, where the Debye length is much shorter than the antibody. To overcome this challenge, double pulse measurements using AlGaN/GaN HEMT biosensors may be utilized, with an electrical double layer approach in which the functionalized gate electrode is spatially separated from the active gate channel area to eliminate these charge screening effects in high ionic strength solutions. This allows the measurements to be performed without any dilution or washing process.

In this disclosure, a disposable cover glass externally integrated with an AlGaN/GaN HEMT is employed to detect the ZIKV. Two metal electrodes were fabricated on the glass: one of them functionalized with antibody and the other one connected to the gate side of the HEMT device. The functionalized electrode was exposed to different concentrations of ZIKV solution. During application of a pulsed voltage to the electrode functionalized with antibody, the time dependent drain currents of HEMT were monitored, and the changes in drain current were used to determine the ZIKV concentrations. A spring-like elastic relaxation model and the Langmuir extension model were used to simulate the dynamic and static drain current responses, respectively, with excellent fits to the experimental data. The dynamic and static drain currents were defined as the time dependent drain current and the drain current at chosen specific time.

Figure 6:
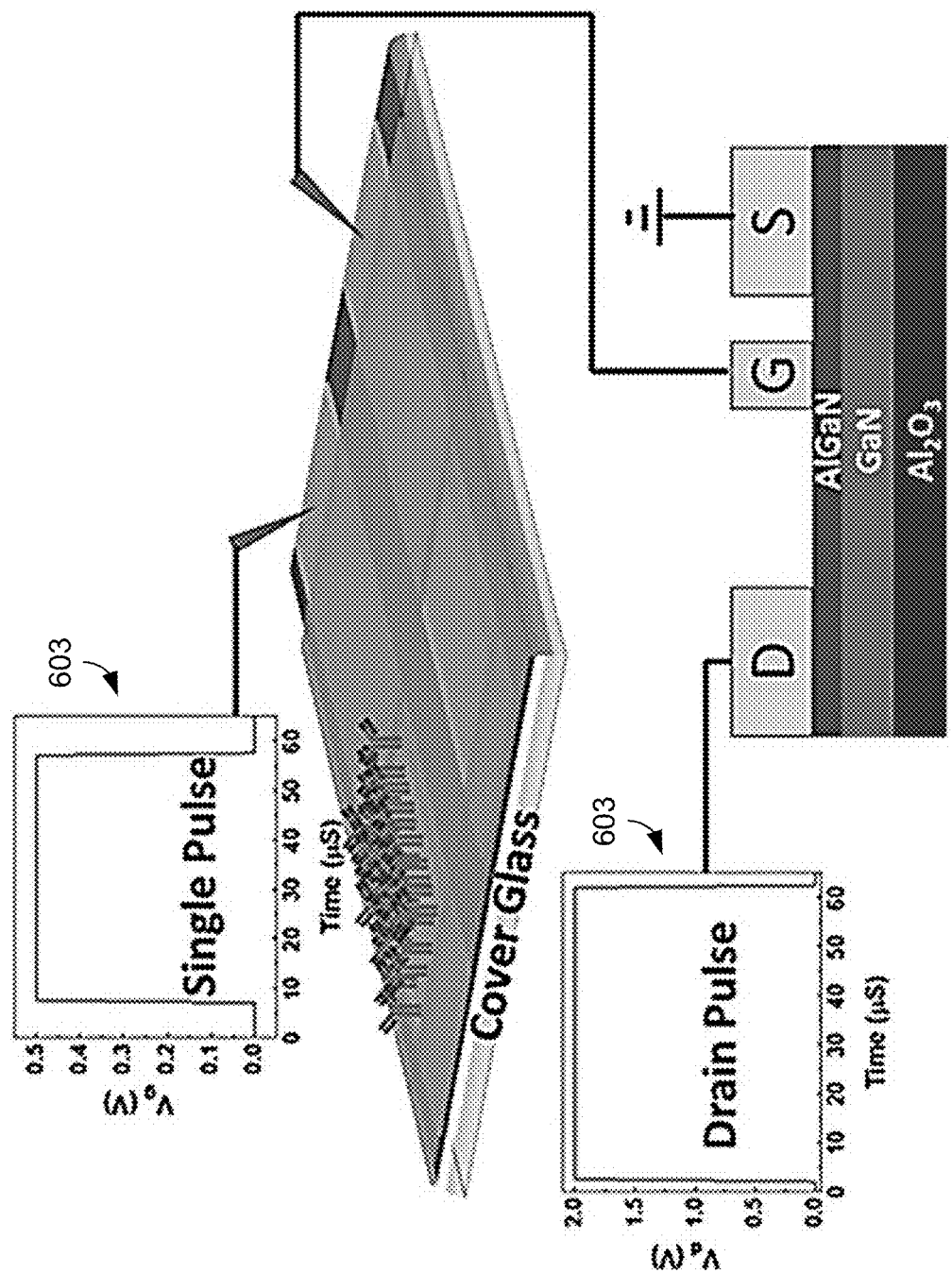
FIG. 6 is a schematic illustrating an example of a cover glass sensor, in accordance with various embodiments of the present disclosure.

Referring to FIG. 6, shown is a schematic of a Zika virus sensor with a cover glass functionalized with Zika antibody in a 100×100 pmt area and separated by 20 μm from a bare electrode externally connected with a HEMT. A 0.5 pulsed gate voltage (VG, 50 μs duration) was applied to the electrode fabricated on the cover glass and functionalized with Zika antibody, while a pulsed drain voltage (VD, 60 μs duration) of 2 V was applied to the drain of HEMT.

FIG. 6 illustrates the cover glass sensor set-up, which comprises an antibody functionalized cover glass and an AlGaN/GaN HEMT. The AlGaN/GaN HEMT structure is grown on a sapphire substrate with a low temperature AlN nucleation layer, 2.2 μm undoped GaN buffer layer, and 25 nm $Al_{0.25}Ga_{0.75}N$ barrier layer by metal organic chemical vapor deposition. Device isolation was achieved with a $Cl_2$/Ar discharge in a Plasma Therm 790 inductively coupled plasma (ICP) system with 200 W ICP power and 50 W rf power at 2 and 13.56 MHz, respectively. The source and drain Ohmic contacts were formed by e-beam evaporation with Ti/Al/Ni/Au (25/125/45/100 nm) with a standard lift-off process, and the contacts were annealed at 850° C. for 45 s. Schottky gate contacts were formed with e-beam deposition Ni/Au (20 nm/80 nm). Ti/Au was used as interconnection metals.

For the cover glass portion, two 100 μm wide metal lines of Ni/Au (20 nm/80 nm) separated by 20 μm were fabricated using e-beam evaporation and standard lift-off. A 100 nm $SiN_x$ passivation layer was deposited with a plasma enhanced chemical vapor deposition system to passivate the metal electrodes, and a 100 μm×100 μm contact window was opened on both metal electrodes with buffered oxide etch (BOE). One of the contact windows was treated with 1 mM of thioglycolic acid (TGA) for 12 h by covering the other contact window with the photoresist. The TGA thiol group strongly interacts with and bonds to the Au surface, which was previously verified by X-ray photoelectron spectroscopy. The excess TGA molecules were rinsed off with de-ionized water, and the photoresist was stripped with acetone. 100 μg/ml Zika antibody solution (recombinant Zika NS1) was introduced to the contact window coated with TGA, and the samples were stored at 4° C. for 2 h. The carboxyl functional group of the TGA molecules reacted to the amines on the Zika antibody. The antibody reacting with the carboxyl functional group was previously studied by atomic force microscopy, which showed the average height of the antibodies of around 4.2 nm. Then, the cover glass was rinsed with deionized (DI) water and 10 nM phosphate-buffered saline (PBS) solution to remove any unbonded Zika antibody molecules.

To test the Zika antigen concentration, the time dependent HEMT drain current was measured at room temperature using a Keysight B1500 parameter analyzer. A Keysight B1530 pulse generator 603 was employed to provide a 60 μs pulsed voltage of 2 V on the drain of the HEMT and a synchronized 50 μs pulsed voltage of 0.5 V on the Zika antibody immobilized electrode with 5 μs delay after biasing the drain electrode with a Keysight B1530 pulse generator 603, as shown in FIG. 6. The target Zika antigen (recombinant Zika Virus NS1) solutions with an isoelectric point of 5.8 were diluted with 2 wt. % Tween 20 and 0.5 wt. % bovine serum albumin (BSA) in pF 7.4 PBS solution with 0.1, 1, 10, or 100 ng/ml concentrations. A buffering time of 5 minutes was employed for the Zika antigen to bind to the recombinant Zika NS1 protein before each target concentration measurement. Five devices of each type were tested, and each data point represents the average of five measurements from each of these devices.

Figure 7:
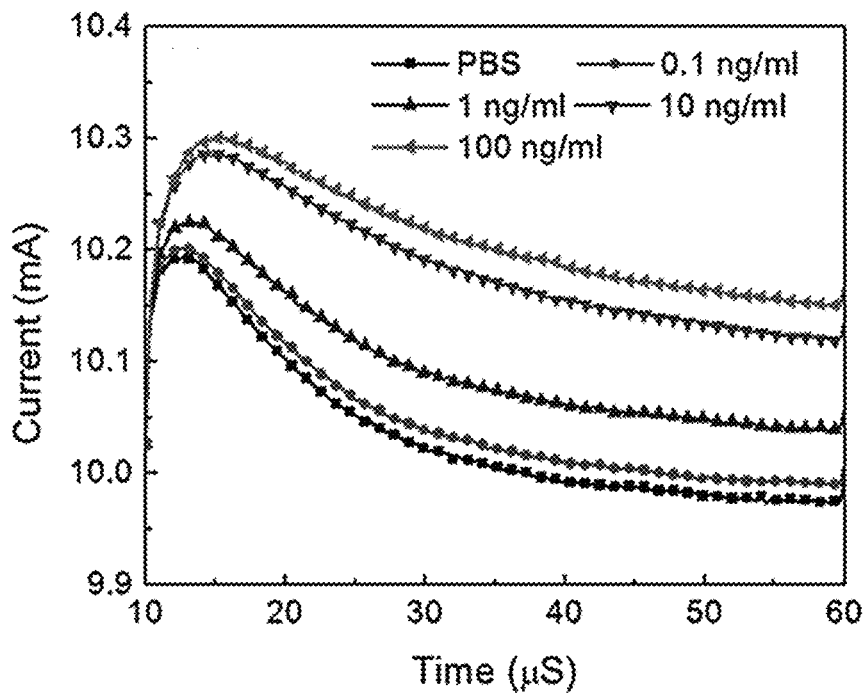
FIG. 7 illustrates examples of drain current response using the cover glass sensor of FIG. 6, in accordance with various embodiments of the present disclosure.

FIG. 7 illustrates the time dependent drain currents for the cover glass exposed to blank 1×PBS, Tween 20, and 1% BSA and such PBS with different antigen concentrations. FIG. 7 shows the time dependent HEMT drain current responses to 0.5 V of 50 μs pulsed voltage applied to the electrode functionalized with the Zika antibody. There were two distinct characteristics observed for the dynamic drain current response after applying +0.5 V pulsed voltage. First, the static drain current increase during the entire period of 50 μs was dependent on the Zika antigen concentration applied on the contact window of the glass sample. For higher Zika antigen concentrations, larger increases of drain current were observed. For the time dependent drain current, within this 50 μs period, the drain current suddenly increased within 5 μs after applying the 0.5 V pulsed voltage and then gradually leveled off.

The higher drain current corresponding to the 50 μs pulsed voltage applied to the electrode functionalized with Zika antibody means that more positive charges are induced on the gate of HEMT due to charge neutralization on the electrodes on the glass, as well as in the PBS or PBS with different concentrations of the antigen solution electrode and the negative charges carried on the antibody and antigen. Since the isoelectric point of the antigen is 5.8 to compare with the isoelectric point of 7.4 for the reference PBS, the antigen would carry negative charges in the PBS with different concentrations of antigen solution applied on the contact windows of the glass.

Figure 8:
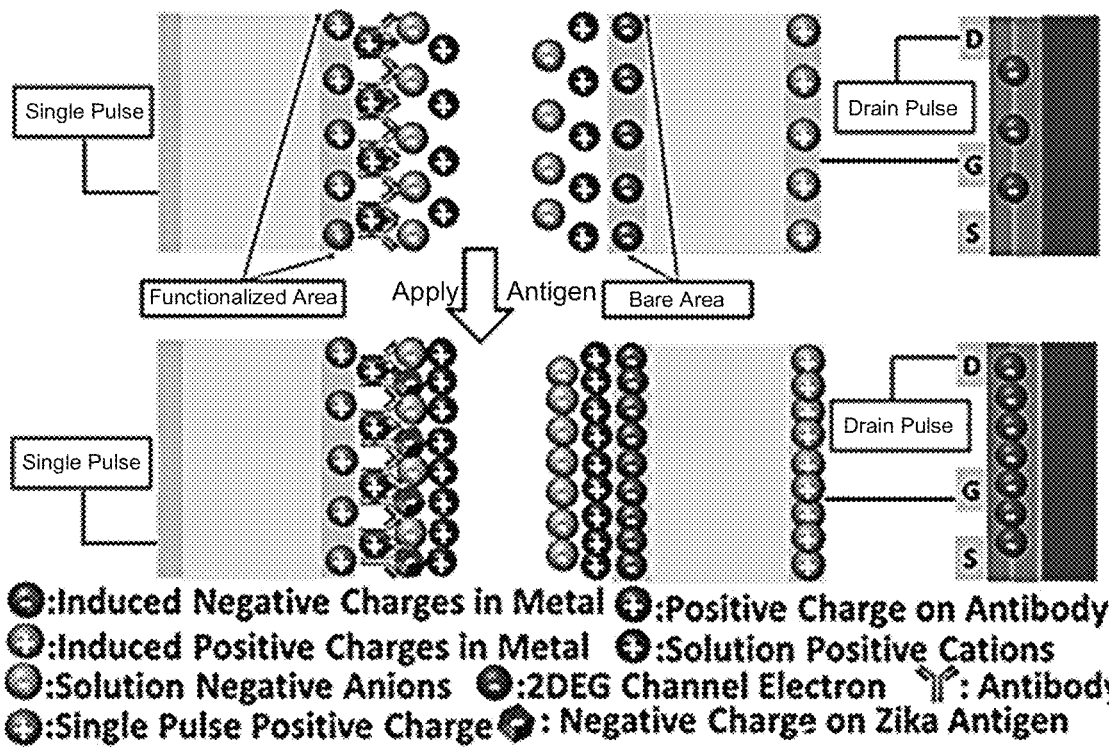
FIG. 8 illustrates an example of a distribution of induced charges on the metal electrode, charges in the solution around the vicinity of the electrode, and negative charges on the antibody and antigen molecules using the cover glass sensor of FIG. 6, in accordance with various embodiments of the present disclosure.

Referring to FIG. 8, shown is a schematic illustrating the distribution of induced charges on the metal electrode, charges in the solution around the vicinity of the electrode, and negative charges on the antibody and antigen molecules. The HEMT structure comprises AlGaN/GaN layers on a sapphire substrate and source (S), drain (D), and gate (G) contacts. As shown in FIG. 8, the opposite-polarity electrical double-layers are induced on both the functionalized and unfunctionalized windows as a result of the positive 0.5V of single pulse and native charges on the antigen. Due to charge neutralization in the PBS or PBS solution with different antigen concentrations, more positive charges in the solution accumulate on the metal electrode contact window without functionalized antibody, and negative charges are induced on the metal electrode next to the solution with more positive charges. Since this metal electrode is externally connected to the gate of HEMT, more positive charges are induced by the negative charges on the metal electrode next to the solution via charge neutralization on the metal. For the PBS solutions applied on the glass sample with higher antigen concentrations, more antigen molecules with negative charge will bind to the antibody molecules. Thus, the drain current increase was proportional to the antigen concentration through charge neutralization in both solution and metal, with more positive charge inducing more positive charge on the gate of HEMT and producing higher drain currents.

Figure 9:
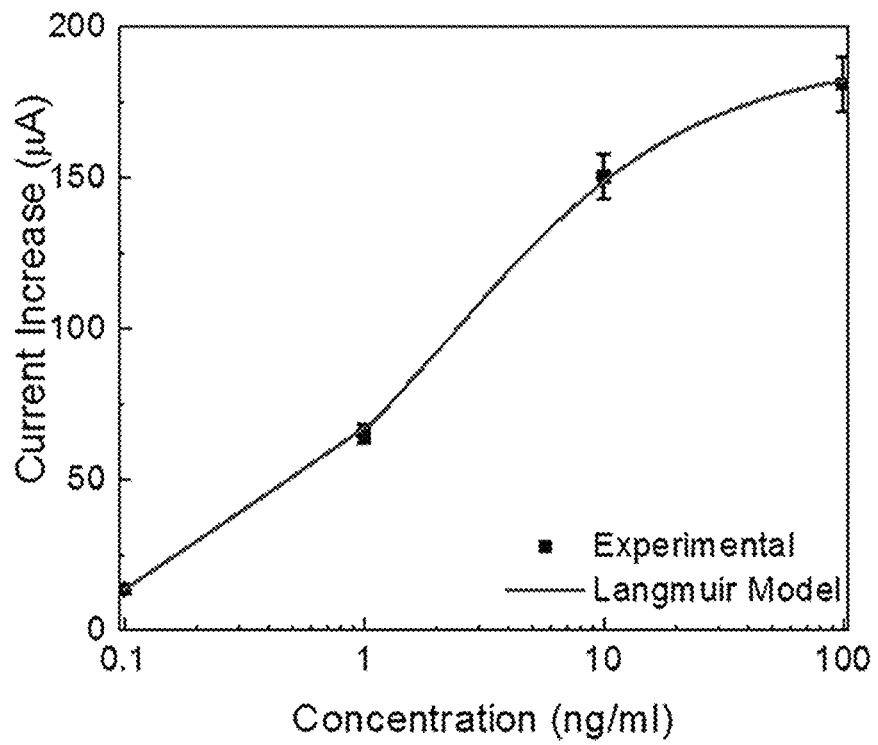
FIG. 9 illustrate experimental values of current with one site binding model fitting using the cover glass sensor of FIG. 6, respectively, in accordance with various embodiments of the present disclosure.

The antigen and antibody binding occurs through active sites on these two protein molecules. This binding process was reversible, and the drain current change of HEMT induced by the different concentrations of antigen solution could be fit with the Langmuir Extension model shown in the following equation:

$$\Delta I = \frac{101 * [C]^{0.87}}{1 + 0.54 * [C]^{0.87}}, \quad (5)$$

where $\Delta I$ is the change in drain current between the target antigen solutions and baseline PBS solution at 50 μs in FIG. 7. [C] is the antigen concentration in ng/ml. FIG. 9 illustrates examples of the drain current increase (data point) for the cover glass exposed to different antigen concentrations (semi-log scale) as compared to the drain current for the cover glass exposed to the blank PBS solution, and the simulated drain current increases with the Langmuir extension model. As shown in FIG. 9, the modeled drain current changes with different concentrations and fits well with the experimental data, with error bars less than 5%.

For the time-dependent drain current, within this 50 μs period, the drain current abruptly increased after applying the 0.5 V pulsed voltage and then gradually leveled off. Since the antigen and antibody molecules carry negative charges, they will be attracted to the electrode functionalized with antibody by the +0.5 V pulsed voltage being applied. Once these molecules reach the electrode, a repelling force builds as a result of the negative charges. These molecules would gradually relax, as shown in FIG. 9. The static drain current increases were induced by the negative charges on the antibody and antigen molecules. The drain current increases when both the antibody and antigen molecules are attracted closer to the metal electrode upon application of the 0.5 V pulsed voltage and then progressively level off as an equilibrium is reached.

The protein structure has a variety of physical interactions with an applied electric-field in terms of stretching, shearing, bending, and contraction with breaking and reforming of hydrogen bonds, local pH changes, and protein side-chain motions. Such transformations of the protein configuration stimulated by the electric-field were modeled with a molecular dynamics simulation technique. The Hookean spring model was employed to simulate the relaxation portion of the time-dependent drain current. The dynamic equation of the mass-spring-damper model is given by:

$$m\frac{d^2x(t)}{dt^2} + \varphi * \frac{dx(t)}{dt} + k * x(t) = 0, \quad (6)$$

where m and k are the protein material properties, φ is the dragging coefficient associated with protein relaxation, t is the time, and x(t) is the stretched distance of the antibody and antigen under a certain electrical field and is proportional to the charges induced on the gate of HEMT. Since the drain current is proportional to the gate voltage of the HEMT or the stretched distance of the antibody and antigen molecules, the solution of Eq. (6) for the stretched distance is directly proportional to the drain current as:

$$I_D(t) = (1 - c^*) * A * \exp\left(-\frac{t[\mu s]}{\tau_1}\right) + c^* * B * \exp\left(-\frac{t[\mu s]}{\tau_2}\right) + E, \quad (7)$$

where $c^*$ is the ratio of antibody bound with antigen to the total available antibody on the functionalized contact window, $\tau_1$ and $\tau_2$ are the relaxation time constants of antibody and antigen molecules, respectively, and A, B, and E are the constants. $c^*$ mainly depends on the antigen concentration, and it can be related to $\Delta I$ through the Langmuir model. The fitting equation for $c^*$ and [C] is as follows:

$$c^* = \frac{0.14 * [C]^{1.33}}{1 + 0.17 * [C]^{1.33}}. \quad (8)$$

Figure 10:
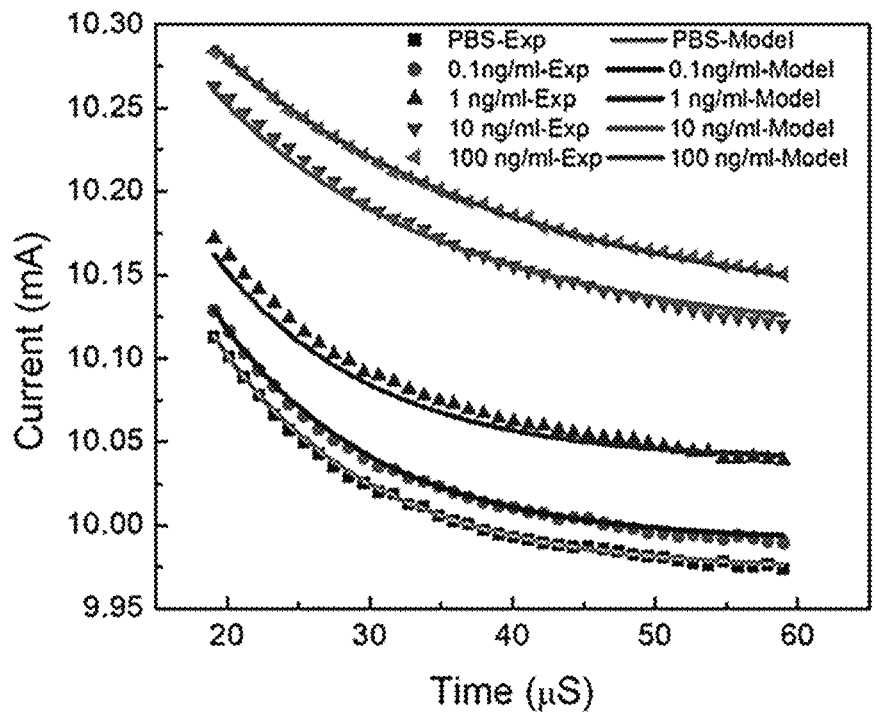
FIG. 10 illustrates examples of dynamic drain current with spring relaxation modeling for the cover glass sensor of FIG. 6, in accordance with various embodiments of the present disclosure.

FIG. 10 illustrates examples of the dynamic drain current (data point) for the cover glass exposed to different antigen concentrations and the simulated drain current with the spring relaxation model. FIG. 10 shows the modeled drain current for PBS solution without antigen and PBS solutions with different antigen concentrations, and the following table lists the simulated time constants and ratio of antibody bound with antigen to the total available antibody.

| Zika Concentration [C] (ng/ml) | $c^*$ | $\tau_1$ (μs) | $\tau_2$ (μs) |
|---|---|---|---|
| 0 (PBS, BSA, Tween 20) | 0.00 | 10.97 | — |
| 0.1 | 0.013 | — | 0.66 |
| 1 | 0.12 | — | 1.01 |
| 10 | 0.67 | — | 22.22 |
| 100 | 0.84 | — | 24.39 |

The table gives the ratio of antibody bound with antigen to the total available antibody on the functionalized contact window, $c^*$, and relaxation time constants of antibody and antigen molecules, $\tau_1$ and $\tau_2$, respectively, as a function of Zika antigen concentration.

As shown in FIG. 10, the simulated time dependent drain current had an excellent fit with the experimental data. There was a 40× difference in the antigen relaxation time constant, $\tau_2$, for the lower (0.66 μs at 0.1 ng/ml) and higher antigen concentrations (24.4 μs at 100 ng/ml), which could be due to additional interactions among antigen molecules for the higher antigen concentrations. Note that the ratio of antibody bound with antigen to the total available antibody on the functionalized contact window increased from 0.013 at 0.1 ng/ml to 0.84 at 100 ng/ml, with the ratio scaling faster than the concentration due to increased interaction probability.

In summary, a rapid, low cost, bio-sensor for ZIKV was demonstrated by integrating a disposable cover glass with metal electrodes with an AlGaN/GaN HEMT. The HEMT is not exposed to any chemicals and can be reused. A wide range of Zika antigens, 0.1-100 ng/ml, were detected. The Langmuir extension model and spring-like elastic relaxation models provided excellent fits to the experimental static and dynamic drain currents upon pulsed biasing of the electrode fabricated on the cover glass and functionalized with Zika antibody. Besides glass slides, plastics and paper can also be used as the disposable functionalized sensor strips.

It should be emphasized that the above-described embodiments of the present disclosure are merely possible examples of implementations set forth for a clear understanding of the principles of the disclosure. Many variations and modifications may be made to the above-described embodiment(s) without departing substantially from the spirit and principles of the disclosure. All such modifications and variations are intended to be included herein within the scope of this disclosure and protected by the following claims.

It should be noted that ratios, concentrations, amounts, and other numerical data may be expressed herein in a range format. It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a concentration range of "about 0.1% to about 5%" should be interpreted to include not only the explicitly recited concentration of about 0.1% to about 5%, but also include individual concentrations (e.g., 1%, 2%, 3%, and 4%) and the sub-ranges (e.g., 0.5%, 1.1%, 2.2%, 3.3%, and 4.4%) within the indicated range. The term "about" can include traditional rounding according to significant figures of numerical values. In addition, the phrase "about 'x' to 'y'" includes "about 'x' to about 'y'".

Therefore, at least the following is claimed:

1. A medical sensor, comprising:
a base structure comprising a functionalized sensing area disposed on a first electrode pad and a reference sensing area disposed on a second electrode pad, the first and second electrode pads disposed on the base structure with the second electrode pad physically separated from the first electrode pad;
a transistor having a gate connected to the second electrode pad of the base structure and a drain, the transistor physically separate from the first electrode pad; and
a pulse generator that generates a drain pulse and a gate pulse synchronized with the drain pulse, the pulse generator comprising a first pulse generator output that supplies the gate pulse and a second pulse generator output that supplies the drain pulse, the first pulse generator output connected to the first electrode pad and the second pulse generator output connected to the drain, where the transistor produces a drain current in response to the synchronized drain and gate pulses applied to the first electrode pad of the base structure and the drain of the transistor, the drain current corresponding to an amount of a target present in a sample disposed on the base structure.

2. The medical sensor of claim 1, wherein the transistor is a GaAs MESFET, an InP FET, a heterojunction bipolar transistor, a Si MOSFET, a SiCMOS transistor, a SiGe FET, a biCMOS transistor or an III-V semiconductor based HEMT.

3. The medical sensor of claim 2, wherein the III-V semiconductor based HEMT is a GaAs, InAlAs or InGaAs based HEMT.

4. The medical sensor of claim 1, wherein the functionalized sensing area is functionalized for antibody-antigens, enzymes, hybridized DNA or RNA, proteins, peptides or aptamers.

5. The medical sensor of claim 1, wherein the transistor is an AlGaN/GaN high electron mobility transistor (HEMT).

6. The medical sensor of claim 1, wherein the functionalized sensing area is functionalized with a troponin antibody.

7. The medical sensor of claim 6, wherein the troponin antibody is bound to the functionalized sensing area by a binding agent disposed on the first electrode pad.

8. The medical sensor of claim 7, wherein the binding agent is thioglycolic acid (TGA, $HSCH_2COOH$).

9. The medical sensor of claim 1, wherein the functionalized sensing area is functionalized with a Zika antibody.

10. The medical sensor of claim 1, wherein the base structure is a glass slide.

11. The medical sensor of claim 1, wherein the base structure is a plastic strip.

12. The medical sensor of claim 1, wherein the base structure is a paper strip.

13. The medical sensor of claim 1, wherein the drain pulse generated by the pulse generator has a first duration and the gate pulse generated by the pulse generator has a second duration less than the first duration, the gate pulse starting a defined delay after the drain pulse starts and ending before the drain pulse ends.

* * * * *